(12) United States Patent
McGovern et al.

(10) Patent No.: US 10,807,928 B2
(45) Date of Patent: *Oct. 20, 2020

(54) RECIRCULATING PROCESS FOR PREPARING ETHYLENE GLYCOL

(71) Applicant: Scientific Design Company, Inc., Little Ferry, NJ (US)

(72) Inventors: Shaun McGovern, Hoboken, NJ (US); Eunice Yamada, Pittstown, NJ (US); Barry Jay Billig, Irvington, NY (US); Chun Chau Chan, Brooklyn, NY (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/399,108

(22) Filed: Apr. 30, 2019

(65) Prior Publication Data

US 2019/0330133 A1 Oct. 31, 2019

Related U.S. Application Data

(60) Provisional application No. 62/664,706, filed on Apr. 30, 2018.

(51) Int. Cl.
*C07C 29/152* (2006.01)
*C07C 29/153* (2006.01)

(52) U.S. Cl.
CPC .......... *C07C 29/152* (2013.01); *C07C 29/153* (2013.01)

(58) Field of Classification Search
CPC ..... C07C 29/10; C07C 29/106; C07C 29/152; C07C 29/153
See application file for complete search history.

(56) References Cited

U.S. PATENT DOCUMENTS

| | | |
|---|---|---|
| 3,028,434 A | 4/1962 | Weisz et al. |
| 3,563,914 A | 2/1971 | Wattimena |
| 3,702,259 A | 11/1972 | Nielsen |
| 3,867,113 A | 2/1975 | Foster et al. |
| 3,957,698 A | 5/1976 | Hatch |
| 4,160,116 A | 7/1979 | Mieno et al. |
| 4,165,440 A | 8/1979 | Kim |
| 4,519,875 A | 5/1985 | Becker et al. |
| 4,761,394 A | 8/1988 | Lauritzen |
| 4,766,105 A | 8/1988 | Lauritzen |

(Continued)

FOREIGN PATENT DOCUMENTS

| | | |
|---|---|---|
| CN | 1208135 A | 2/1999 |
| CN | 103709001 A | 4/2014 |

(Continued)

OTHER PUBLICATIONS

International Search Report dated Aug. 12, 2019, received in International Application No. PCT/US2019/029830.

(Continued)

*Primary Examiner* — Yate' K Cutliff

(74) *Attorney, Agent, or Firm* — Scully Scott Murphy and Presser

(57) ABSTRACT

An improved catalytic hydration process that includes a catalytic hydration reaction section containing adiabatic reactors with ion exchange resin catalyst and which maintains low resin swelling and excellent selectivity while also reducing process complexity and increasing versatility.

17 Claims, 3 Drawing Sheets

(56) References Cited

U.S. PATENT DOCUMENTS

| | | | |
|---|---|---|---|
| 4,778,567 | A | 10/1988 | Kakimoto et al. |
| 4,875,909 | A | 10/1989 | Kakimoto et al. |
| 4,908,343 | A | 3/1990 | Bhasin |
| 5,011,807 | A | 4/1991 | Hayden et al. |
| 5,057,481 | A | 10/1991 | Bhasin |
| 5,099,041 | A | 3/1992 | Hayden et al. |
| 5,102,848 | A | 4/1992 | Soo et al. |
| 5,187,140 | A | 2/1993 | Thorsteinson et al. |
| 5,407,888 | A | 4/1995 | Herzog et al. |
| 5,763,691 | A | 6/1998 | Kawabe et al. |
| 5,945,568 | A | 8/1999 | Nagata et al. |
| 6,160,187 | A * | 12/2000 | Strickler ............... C07C 29/106 568/867 |
| 6,211,419 | B1 | 4/2001 | Strickler et al. |
| 7,453,015 | B2 | 11/2008 | Van Kruchten et al. |
| 7,663,005 | B2 | 2/2010 | Crudge et al. |
| 7,683,221 | B2 | 3/2010 | Powell et al. |
| 8,183,400 | B2 | 5/2012 | Szul et al. |
| 2002/0082456 | A1* | 6/2002 | Van Kruchten ....... C07C 29/106 568/867 |
| 2005/0119510 | A1 | 6/2005 | Boons et al. |
| 2006/0161026 | A1 | 7/2006 | Van Kruchten |
| 2006/0183927 | A1 | 8/2006 | Billig et al. |
| 2007/0037991 | A1 | 2/2007 | Rizkalla |
| 2017/0298035 | A1* | 10/2017 | Olthof ................... B01D 3/009 |

FOREIGN PATENT DOCUMENTS

| | | |
|---|---|---|
| CN | 104974115 A | 10/2015 |
| EP | 0123700 A1 | 11/1984 |
| EP | 0123709 A1 | 11/1984 |
| EP | 1828086 B1 | 10/2009 |
| EP | 2121646 B1 | 2/2011 |
| JP | 2010528113 A | 8/2010 |
| WO | 0035840 A1 | 6/2000 |
| WO | 2006072766 A1 | 7/2006 |
| WO | 2008150338 A1 | 12/2008 |
| WO | 2009105252 A1 | 8/2009 |
| WO | 2017178418 A1 | 10/2017 |

OTHER PUBLICATIONS

International Search Report dated Aug. 13, 2019, received in International Application No. PCT/US2019/029820.

International Search Report dated Aug. 13, 2019, received in International Application No. PCT/US2019/029818.

International Search Report dated Aug. 16, 2019, received in International Application No. PCT/US2019/029825.

Shvets, V. F., et al., "The Model of Catalytic Reactor of Ethylene Glycol Production", Organic Process Research & Development, Published on web Nov. 2, 2005, pp. 768-773, vol. 9, No. 6.

Office Action dated Nov. 25, 2019 received in U.S. Appl. No. 16/398,975.

Othmer, D. F., et al., "Glycol Production—Hydration of Ethylene Oxide", Industrial and Engineering Chemistry, Sep. 1958, pp. 1235-1244, vol. 50, No. 9.

Van Hal, J. W., et al., "Investigation of three types of catalysts for the hydration of ethylene oxide (EO) to monoethylene glycol (MEG)", Catalysis Today, Available online Mar. 19, 2007, pp. 310-315, 123.

Office Action dated Dec. 13, 2019 received in U.S. Appl. No. 16/399,045.

* cited by examiner

RECIRCULATING PROCESS FOR PREPARING ETHYLENE GLYCOL

CROSS REFERENCE TO RELATED APPLICATION

The present invention claims the benefit of U.S. Provisional Patent Application No. 62/664,706 filed Apr. 30, 2018, the entire content and disclosure of which is incorporated herein by reference.

FIELD OF THE INVENTION

The present invention relates to a method for the oxidation of ethylene into ethylene oxide and the hydration of ethylene oxide into ethylene glycol.

BACKGROUND OF THE INVENTION

The role of ethylene glycol in society has advanced considerably from the time when shortly after its first synthesis the molecule's properties became the subject of a fierce dispute between two giants of early organic chemistry, Adolphe Wurtz and Hermann Kolbe. In particular, Wurtz and Kolbe disputed ethylene glycol's functionality and chemical formula among the still emerging understanding of alcohol homologs, which were key to Kolbe's greater theories about chemical structure. The laboratory soon became a proxy war of the rising industrial and technical might of the growing rivalry between Germany and France with both countries devoting considerable resources to the scientific investigation and Wurtz's wizardry at chemical synthesis giving France a considerable advantage. The dispute was ended only by resort to arms when Bismarck's German Confederation annexed Wurtz's Alsatian homeland as a result of the Franco-Prussian war and thus, essentially turned an international dispute into a domestic one.

Today, interest in ethylene glycol is more peaceful but all the more competitive because ethylene glycol is one of the most widely produced organic chemicals. Since large scale industrial production of ethylene glycol began on the eve of the First World War, dramatic increases in the use of the internal combustion engine to power automobiles and other vehicles has spurred demand for ethylene glycol as a coolant and antifreeze. Since then, the increase in the production of ethylene glycol has only accelerated, so that by 2017, the estimated worldwide production of ethylene glycol was in excess of 25 billion tons.

Ethylene glycol is typically prepared as one of many of the derivatives of ethylene oxide, and though other production routes are available, most is produced from ethylene oxide in a liquid phase non-catalytic thermal hydration process. Because ethylene oxide reacts with ethylene glycols more readily than it reacts with water it is inevitable that a mixture of monoethylene glycol (MEG), as well as higher glycol coproducts, such as diethylene glycol (DEG), triethylene glycol (TEG) and yet still higher ethylene glycols will be formed. Although these higher glycols have considerable economic value, many producers and plant operators wish to avoid producing them because the end-user market for these products is not as well developed and it may be difficult to find and distribute these higher glycols to industrial consumers who have a need for them.

In order to suppress the reaction between product glycol and ethylene oxide and thereby reduce the formation of these higher glycols, conventional non-catalytic hydration is performed with an amount of water that far exceeds the stoichiometric amount of water for the hydration of ethylene oxide to ethylene glycol, e.g., 15 to 40 moles of water per mole of ethylene oxide. This addition of excess water is effective at balancing the kinetically-favored competing reaction between product glycol and ethylene oxide, which as mentioned above competes with the hydration of ethylene oxide to monoethylene glycol. However, while effective at suppressing the production of higher ethylene glycols, using a large excess of water relative to ethylene oxide presents a problem for the plant operator in removing these large excesses of unreacted water because such removal is energy intensive and requires large-scale evaporation/distillation facilities. Accordingly, there has been intensive research into alternatives to the standard thermal hydration of ethylene oxide for the production of ethylene glycol.

One early example of an alternative to conventional thermal hydration is the homogeneous catalytic hydration of ethylene oxide to monoethylene glycol. The earliest examples of this approach included the homogeneous catalysis of sulfuric acid and their associated salts (see Othmer, D. F. and Thakar, M. S., Glycol Production-Hydration of Ethylene Oxide. Ind. Eng. Chem. 1958, 50, 1235). European Patent No. 0 123 700 described refinements of these earlier generations of acid catalysts by treating them with, e.g., ethylamines to partially neutralize them in the hope of improving the selectivity of the hydration reaction to monoethylene glycol. Since then other salts have been proposed for homogeneous systems, such as quaternary phosphonium salts as described in U.S. Pat. No. 4,160,116 and metallate and bicarbonate salts as described in U.S. Pat. No. 7,683,221. Increasingly creative combinations of organic species such as EDTA and Salen compounds have also been proposed as homogeneous catalysts (see Hal, J. W., Ledford, J. S., and Zhang, X., Catalysis Today 123 (2007), 310-315).

Homogeneous catalyst systems are often utilized in a two-step process for manufacturing ethylene glycol, see e.g., U.S. Pat. No. 4,519,875 in which ethylene oxide is first reacted with carbon dioxide to manufacture ethylene carbonate, which is then hydrolyzed to ethylene glycol, with typically the same catalyst being used in both steps. Following this pioneering patent, continued research has produced incremental refinements in the two-step process. For example, in U.S. Pat. No. 5,763,691, the carbonation reaction is catalyzed in the ethylene oxide absorbate in the presence of a halogenated organic phosphonium salt carbonation catalyst. Additional research has considerably expanded the scope of known catalysts; see for example macrocyclic chelating compounds ("crown ethers") described in U.S. Pat. No. 7,453,015.

While homogeneous catalysts improved the selectivity of the hydration reaction towards ethylene glycol compared to non-catalytic hydration, homogeneous catalysts have drawbacks that more than offset these improvements. In particular, the glycol product solution contains soluble or suspended homogeneous catalyst—essentially contaminating the product with the catalyst that is detrimental to product quality as well as highly corrosive as, for example, in the case of acid catalysts. Thus, an additional step of separating the homogeneous catalyst from the glycol product solution is necessary increasing the cost and complexity of the process is required. For example, while U.S. Pat. No. 5,763,691 mentioned above seeks to simplify the two-step ethylene glycol manufacturing by reacting the ethylene oxide and carbon dioxide in the absorbate, the patent still requires a separate distillation step for removing the carbonation catalyst.

This process complexity brings with it the additional flaw that it is neither very versatile nor flexible. For example, the process lacks the flexibility to be operated partially catalytically, i.e., in a mixed catalytic and non-catalytic mode—which would allow more higher glycols to be produced should the operator so desire and would also accommodate the plant in case of some logistical or operational upset where it was not capable of operating in a catalytic mode, for example when sufficient catalyst is not available. The two-step hydration process also lacks the versatility to be used both for new plants and revamps. The two-step hydration process can be used only for new plants and cannot be used for revamps because in the case of revamps it would be necessary to remove and replace the entire "back-end," making such a revamp cost-prohibitive. A drawback of the two-step hydration process is the need to inventory concentrated ethylene oxide (greater than 70% concentration) for the production of the ethylene carbonate intermediate in the first step of the process. The carbonation reaction in the first step is conducted by bubbling carbon dioxide into this concentrated liquid ethylene oxide solution at high temperature and pressure (e.g., greater than 1.6 MPa). The large volume of concentrated ethylene oxide requires considerable additional measures (e.g., the provisioning of liquid cold storage) to prevent reactions or events that could result in ignition, combustion, deflagration, detonation or explosion of any gas stream, but especially those containing higher than typical concentrations of ethylene oxide.

Unsurprisingly, given the aforementioned drawbacks of both non-catalytic and homogeneous catalyzed hydration systems, heterogeneous catalysis using solid or supported catalysts has also been investigated. Those looking for the benefits of higher-selectivity of catalytic hydration without the aforementioned disadvantages have turned their attention toward heterogeneous catalyst systems. Because heterogeneous catalysts are not absorbed into the liquid phase reaction or product solutions, do not contaminate products solutions, do not require a separation step, and facilitate continuous operation of the hydration reactor there has been considerable interest in them.

A variety of solid materials have been proposed as heterogeneous catalysts for hydration. This list include zeolites such as those described by U.S. Pat. No. 3,028,434 as well as amorphous aluminosilicates, solid base and supported acid catalysts such as those disclosed by U.S. Pat. No. 4,165,440. Ion exchange resins have also been proposed with partially amine neutralized sulfonic acid styrene-divinyl benzene resin described in EP 0 123 709; quaternary phosphonium ion exchange resin catalysts, see PCT Publication WO 2000/35840; and strong base ion exchange resins as summarized by U.S. Pat. No. 6,211,419 being among the first ion exchange resins proposed to catalyze the reaction of water and ethylene oxide. More recent publications have expanded the field to wide swaths of anion exchange resins, see e.g., CN Patent No. 1208135.

While strong results have been achieved using heterogeneous ion exchange resin catalysts, there are also certain disadvantages to their use. In particular, ion exchange resin have limited tolerance to heat, so that under typical reaction conditions over long service times the resins experience swelling leading to deactivation. Swelling, which results from internal polymerization within the resin bed and the overall buildup of high molecular weight byproducts, is a serious issue that is the essential limiting factor in the lifespan of an ion exchange resin. Resins typically experience some reversible swelling during operation as they are exposed to solvents; however, through careful management this swelling can be mitigated and the effective life of the ion exchange resin extended. However, exposure of the ion exchange resin to ethylene oxide can cause a more problematic and irreversible swelling of the resin—especially when such exposure occurs at the higher temperatures of the hydration reactor, which as mentioned above may be outside the range of temperatures that the resin can satisfactorily tolerate.

Swelling is not only a problem in itself but can also reduce efficiency and complicate the catalytic hydration process; for example, when the excess swelling requires that the resin be replaced and thus, the catalytic hydration unit in which it is contained taken offline. Various attempts have been made to address these difficulties, including attempts to find resins less prone to swelling under typical operating conditions and in addition developing various process modifications the attempt to either improve performance as well as or in addition to reducing swelling. For example, EP Patent No. 1 828 086 discloses the use of "guard beds" designed to remove impurities that purportedly can cause resin swelling, but such efforts have been ineffectual.

Rather than protecting the resins with a guard bed to attempt to minimize swelling, another more successful approach outlined in PCT Publication WO2008/150338 seeks not to protect the resin but instead facilitate the process of removing the ion exchange resin that has exceeded its usable life by the hitherto unsuggested operation of the catalytic reactor in an upflow mode, which expands the catalyst bed, allows for segregation of the catalyst particles by size and thereby the selective removal of swollen particles. A still further approach is that shown in U.S. Pat. No. 6,160,187, which asserts that reductions in swelling can be obtained under adiabatic reaction conditions and the use of an adiabatic reactor. However, the examples contained in the '187 Patent did not actually demonstrate any improvement in swelling performance of the resins, nor have there been subsequent developments of adiabatic operation, whose development has been neglected.

Accordingly, while there have been several promising developments in individual aspects of heterogeneous catalytic hydration, there remains a considerable need for further improvements of catalytic hydration under adiabatic process conditions.

BRIEF SUMMARY OF THE INVENTION

The present invention relates to a liquid phase catalytic hydration of ethylene oxide process for the production of mono ethylene glycol (MEG) including: providing an ethylene oxide-water solution containing ethylene oxide and water; combining the catalytic hydration feedstream with a recirculation split stream to form a first reactor inlet stream; supplying the first reactor inlet stream to an inlet of a first adiabatic reactor, the inlet of the first adiabatic reactor being at a first inlet temperature; reacting the ethylene oxide and water in the presence of a first ion exchange resin catalyst in the first adiabatic reactor to thereby produce an effluent stream containing water, ethylene glycol, and unreacted ethylene oxide; further combining the effluent stream with a recirculation supply stream to form a combined stream containing water, ethylene glycol and unreacted ethylene oxide; supplying the combined stream to an inlet of a second adiabatic reactor, the inlet of the second adiabatic reactor being at a second inlet temperature; reacting ethylene oxide and water in the presence of a second ion exchange resin catalyst in the second adiabatic reactor to thereby produce a second reactor effluent stream containing water, ethylene glycol, and unreacted ethylene oxide; compressing the second reactor effluent stream; dividing the second reactor effluent stream into a recirculation stream and a forward stream; dividing the recirculation stream into the split recirculation stream and the supply recirculation stream; supplying the forward stream as the pipe reactor feedstream to a non-catalytic pipe reactor reactor to produce a product stream wherein the total concentration of DEG, TEG and higher glycols in the product stream is greater than the total concentration of DEG, TEG and higher glycols in the forward stream.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawing.

DETAILED DESCRIPTION OF THE INVENTION

Figure 1:
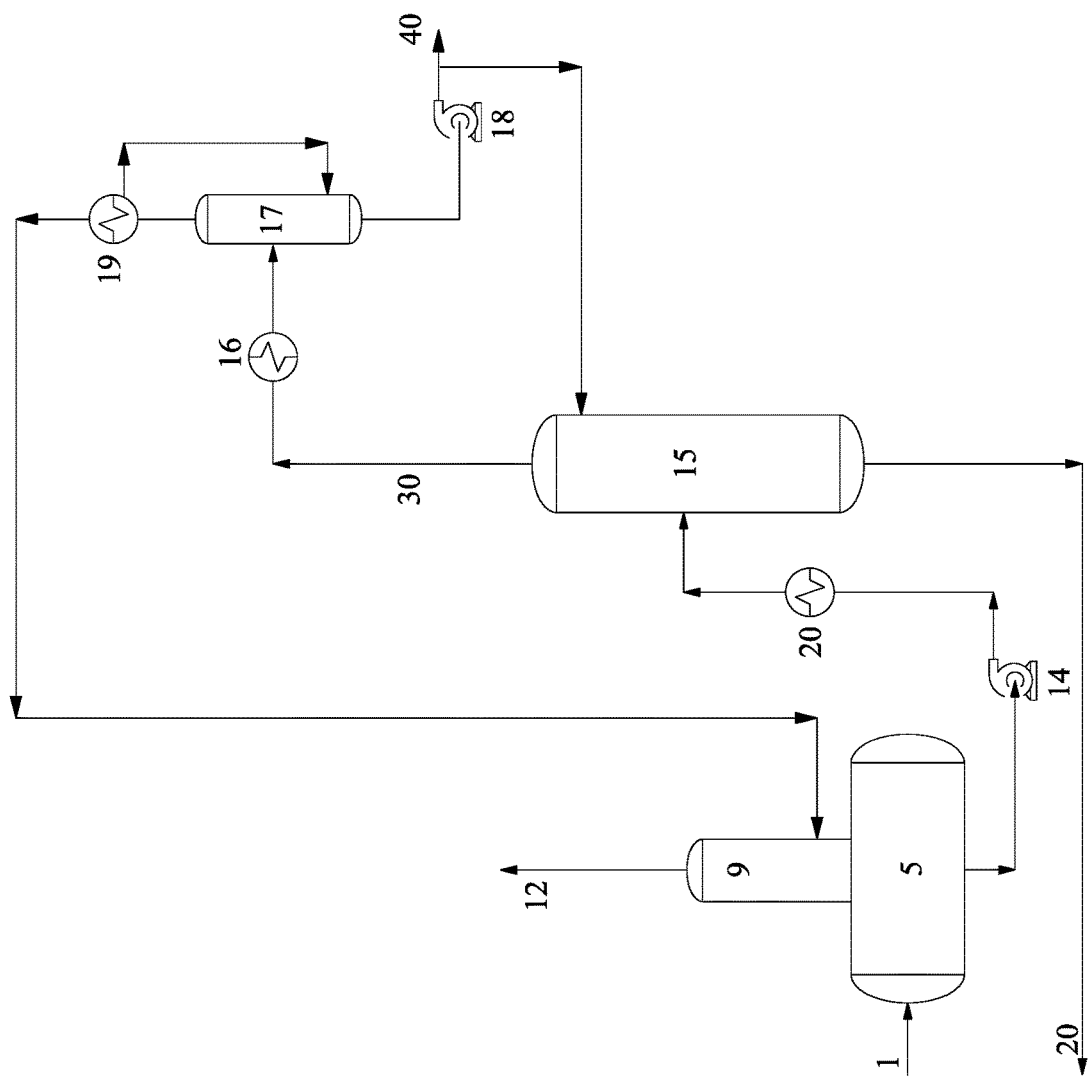
FIG. 1 is a schematic flow sheet for a process for preparing a concentrated ethylene oxide stream as incorporated in the present invention.

All parts, percentages and ratios used herein are expressed by volume unless otherwise specified. All pressures are absolute. All documents cited herein are incorporated by reference.

By "water" it is meant any kind of water suitable for use in chemical and petrochemical processing, including deionized, demineralized, industrial, potable and distilled water. Condensate of steam and condensate obtained from the dehydration and evaporation section of the glycol manufacture process may also be used.

By the present invention, an improved adiabatic catalytic hydration process has been developed in which catalyst swelling is reduced, process flexibility is considerably improved, and the process is configured such that it can be advantageously employed to revamp a non-catalytic process to a catalytic one. A particular advantage of the present invention is that a series of adiabatic reactors are used. Conventionally, the non-catalytic hydration reaction is carried out in a single adiabatic reactor without regard to the outlet, or maximum temperature of the reactor. Such operation could pose particular hazards for the ion exchange resins of the present invention since temperatures outside the temperature range designated for such resins can increase swelling and reduce catalyst life as discussed above.

Rather than use these single-stage adiabatic reactors and the disadvantages which accompany them (such as high temperature in the presence of the catalyst), the present invention instead makes use of multi-stage adiabatic reactors arranged in series. Since no heat is removed in the adiabatic reactor, the temperature of the effluent exceeds the temperature of the feed, and the heat of reaction must be removed from the effluent by a coolant after each stage. This is particularly important to prevent the aforementioned resin swelling and to prevent excessive non-catalytic reaction of product glycols with ethylene oxide to higher glycols. In the present invention, these problems are addressed by providing a catalytic hydration reaction section with two or more adiabatic reactors in series with recirculation and cooling of the reactor effluent to control the reactor temperature. The external cooling removes the heat of reaction of the effluent, reducing its temperature so that it may be recycled to one or more reactor feeds such that reactor temperatures do not exceed a target maximum value. Moreover, from a process perspective cooling with external heat exchangers is easier and less complicated than configuring the appropriate duty for isothermal reactors and can be adjusted to absorb normal fluctuations in the process and maintain the performance of the catalytic reactors. Thus, the use of a series of adiabatic reactors with external coolers such as this improves process versatility and heat removal efficiency. A secondary benefit is that the process allows for a revamping or retrofitting of a conventional non-catalytic hydration process into a catalytic one, as will be described in greater detail below.

In the present invention these benefits are achieved while still preserving the high selectivity of preceding catalytic hydration systems to monoethylene glycol. In each adiabatic reactor bed, ethylene oxide and water react in the presence of a heterogeneous catalyst (such as ion-exchange resin) to form monoethylene glycol with at least 98% of the ethylene oxide converted into monoethylene glycol, with only small percentages being converted into higher glycols like diethylene glycol or triethylene glycol.

Thus, by the present invention an improved process scheme has been developed that includes a catalytic hydration reaction section containing adiabatic reactors in series, which maintains low resin swelling and excellent selectivity while also reducing process complexity and increasing versatility.

This catalytic hydration reaction section (also "reaction section") prepared according to the present invention as described above is shown as 25 in FIG. 2 and will be described in greater detail below. The reaction section 25 is fed with, among other feed streams, a liquid cold feed stream conduit 40, which is highly enriched with ethylene oxide and which is provided at pressures high enough to keep ethylene oxide in liquid. The reaction section 25 includes a finishing adiabatic non-catalyzed thermal EO hydrolysis reactor 26, which assures total conversion of remaining unconverted EO (present in the last adiabatic reactor effluent of the reactor train 22) to ppm levels, reducing the total required catalytic reactor volume of reactor train 22 significantly.

Any suitable means for generating this liquid feed stream which is highly enriched with ethylene oxide is applicable to the present inventive process for catalytically producing ethylene glycol. One suitable means for doing this is the direct two-stage flash absorber-stripper section shown in FIG. 1. FIG. 2 shows the communication between absorber-stripper section 1 and the reaction section 25 that has been prepared according to the present invention. A process for preparing ethylene oxide with reference to this direct two-stage flash absorber-stripper section will now be described in more detail.

Ethylene oxide is produced by continuously contacting an oxygen-containing gas with an olefin, preferably ethylene, in the presence of an ethylene oxide ("epoxidation") catalyst (described in greater detail below). Oxygen may be supplied to the reaction in substantially pure molecular form or in a mixture such as air. By way of example, typical reactant feed mixtures under operating conditions may contain from about 0.5% to about 45%, preferably about 5% to about 30% of ethylene and from about 3% to about 15% oxygen, with the balance comprising comparatively inert materials including such substances as carbon dioxide, water, inert gases, other hydrocarbons, and the reaction moderators described herein. Non-limiting examples of inert gases include nitrogen, argon, helium and mixtures thereof. Non-limiting examples of the other hydrocarbons include methane, ethane, propane and mixtures thereof. Carbon dioxide and water are byproducts of the epoxidation process as well as common contaminants in the feed gases. Both have adverse effects on the catalyst, so the concentrations of these components are usually kept at a minimum.

Also present in the reaction, as previously mentioned, are one or more reaction moderators, non-limiting examples of which include organic halogen-containing compounds such as $C_1$ to $C_8$ halohydrocarbons; especially preferred are chloride-containing moderators such as methyl chloride, ethyl chloride, ethylene dichloride, vinyl chloride or mixtures thereof. Controlling chloride concentration level is particularly important with rhenium-containing catalysts.

As mentioned above, a usual method for the ethylene epoxidation process comprises the vapor-phase oxidation of ethylene with molecular oxygen, in the presence of an epoxidation catalyst, in a fixed-bed tubular reactor. Conventional, commercial fixed-bed ethylene-oxide reactors are typically in the form of a plurality of parallel elongated tubes (in a suitable shell) approximately 0.7 to 2.7 inches O.D. and 0.5 to 2.5 inches I.D. and 15-53 feet long, each filled and packed with catalyst. The reaction feed mixture (described above) is introduced into these tubes, and the resulting reactor effluent gas contains ethylene oxide, un-used reactants, and byproducts.

For purposes of illustration only, the following are conditions that are often used in current commercial ethylene oxide reactor units: a gas hourly space velocity (GHSV) of 1500-10,000 $h^{-1}$, a reactor inlet pressure of 150-400 psig, a coolant temperature of 180-315° C., an oxygen conversion level of 10-60%, and an EO production rate (work rate) of 7-20 lbs. EO/cu·ft. catalyst/hr. The feed composition in the reactor inlet after the completion of start-up and during normal operation typically comprises (by volume %) 1-40% ethylene, 3-12% $O_2$; 0.3% to 20%, preferably 0.3 to 5%, more preferably 0.3 to 1% of $CO_2$; 0-3% ethane, an amount of one or more chloride moderators, which are described herein; and the balance of the feed being comprised of argon, methane, nitrogen or mixtures thereof.

Typical operating conditions for the ethylene epoxidation process involve temperatures in the range from about 180° C. to about 330° C., and preferably, from about 200° C. to about 325° C., and more preferably from about 225° C. to about 280° C. The operating pressure may vary from about atmospheric pressure to about 30 atmospheres, depending on the mass velocity and productivity desired. Higher pressures may be employed within the scope of the invention. Residence times in commercial-scale reactors are generally on the order of about 2 to about 20 seconds.

The reactor effluent exits through the reactor outlet, is cooled and in a preferred embodiment flows to the EO scrubbing column, where the reactor effluent is contacted with recirculated lean cycle water to absorb the ethylene oxide as well as several "light" solutes contained the reactor effluent.

Figure 2:
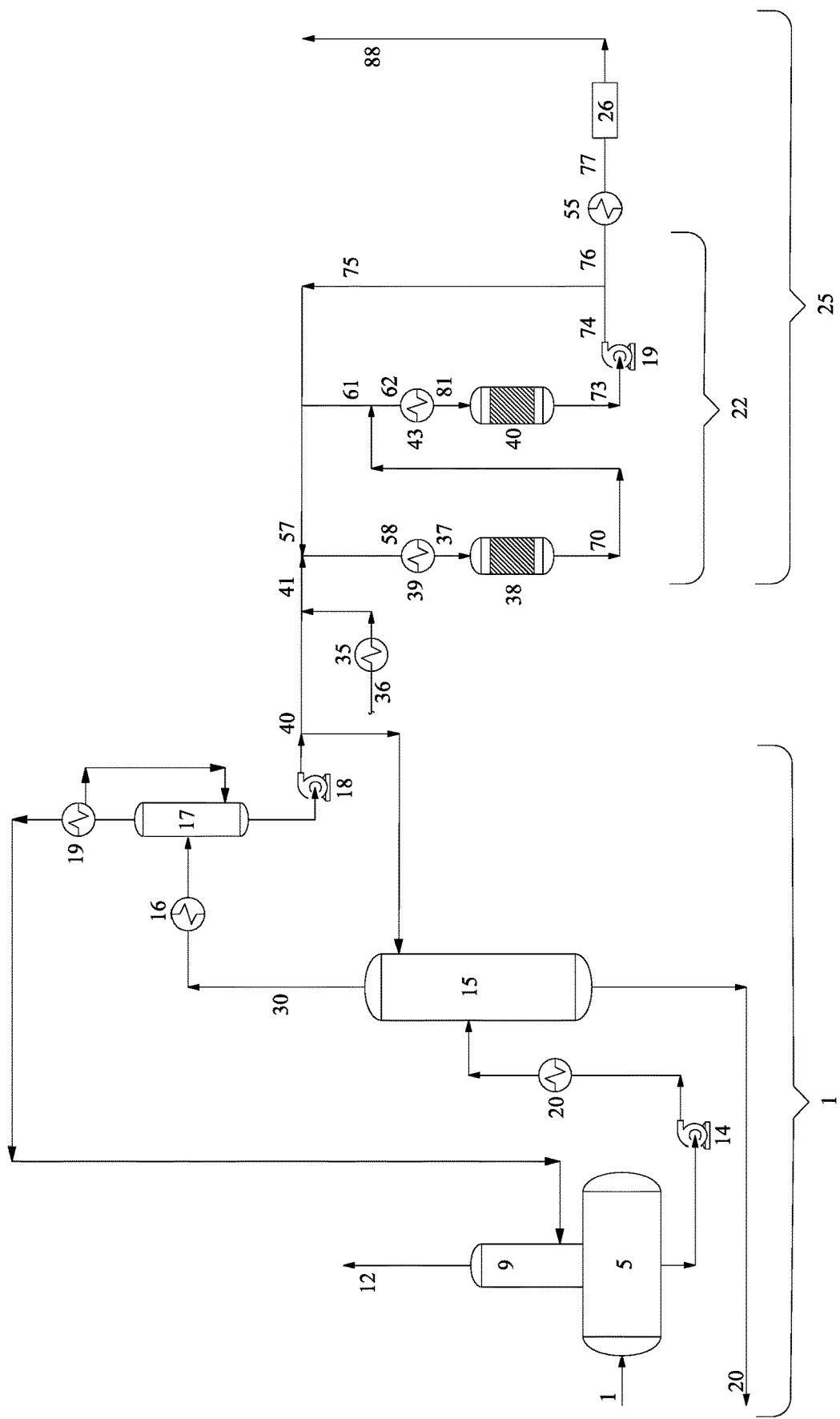
FIGS. 2-3 are schematic flow sheets for process embodiments for preparing ethylene glycol according to the present invention.

In FIG. 1 the scrubbing column liquids (hereinafter referred to as the "rich cycle water" stream) flows through conduit 1 and is supplied to a flash drum 5. The rich cycle water stream is an aqueous stream comprising 1.0 mol % to 4 mol % ethylene oxide with some dissolved light gases such as methane, ethylene and others. This rich cycle water stream is supplied at a pressure of preferably between about 0.4 MPa to about 0.6 MPa to the flash drum 5. An absorber unit 9 is permanently and directly and permanently affixed to the top of the flash drum 5 and an opening is provided in the flash drum for communication with the absorber 9. In the present invention the pressure in both the flash drum 5 and absorber 9 assembly is maintained within a sufficient range so that when the rich cycle water enters the flash drum 5 the "light" gases that are dissolved in the rich cycle water that have a volatility greater than that of ethylene oxide flash out of rich cycle water on entering the flash drum 5 and the light gas vapor is directed by pressure differential between the flash drum 5 and the absorber 9 to rise upwardly through the opening into the absorber 9 to form the overhead of the absorber 9, while the ethylene oxide solute stays largely solubilized within the rich cycle water stream in the liquid bottoms of the flash drum 5. These more volatile "light" gases include the aforementioned inert, unreacted or byproduct gas rich cycle water solutes (In addition, traces of ethylene oxide may also vaporize with the more volatile light gases in the rich cycle water stream.) The small amounts of ethylene oxide that effervesce out of the rich cycle water and rise into the absorber 9 with the light gas solute vapor may be recovered by an downwardly-moving wash stream (not shown) to absorb and recover the upwardly moving ethylene oxide).

As mentioned above, the absorber 9 is directly and permanently affixed to the top surface of the flash drum 5, by for example, welding. The absorber 9 is affixed to the flash drum 5 in the same manner as a still-column and reboiler configuration well-known to those skilled in the art. More specifically, the absorber 9 is affixed to the flash drum 5 along the longitudinal axis of the flash drum 5 but is preferably fixed at the midpoint of the longitudinal axis. The cross-section of the absorber 9 matches the shape of the opening in the flash drum 5 over which the absorber 9 is affixed and which allows communication between the flash drum 5 and the absorber 9. The cross-section of the absorber and the shape of the opening in the flash drum 5 have the same matching shape and that shape may be any shape between a circle and an ellipse, between an eccentricity of 0 and an eccentricity of 1. The opening in the flash drum 5 and the absorber 9 are aligned so that the center of the opening is collinear with the center of the absorber 9. Configuring the opening in the flash drum 5 and the shape of the absorber 9 and their respective alignments ensures that there is proper fluid communication between these two elements. The absorber 9 is preferably welded flush to the inner diameter of the opening made in the flash drum 5 so that the outer diameter of the absorber 9 is flush with the diameter of the opening in the flash drum 5.

In order to ensure the balance between flashing the more volatile "light" solutes while maintaining high solubility of ethylene oxide in the rich cycle water, the pressure in the flash drum 5 is maintained at about 0.1 MPa to about 0.3 MPa and the pressure in the absorber 9 to which there is direct communication is just slightly lower than the pressure in the flash drum 5. The temperature of the gases at the top of the absorber 9 is from about 30° C. to about 45° C., while the temperature in the flash drum 5 is from about 50° C. to about 60° C.

The overhead components of the absorber 9 are returned through conduit 12 to the upstream reaction section (not shown) as possible recycle to the reactor. The rich cycle water flows as liquid bottoms from the flash drum 5 through pump 14 and through optional heat exchanger 20 (which preheats the stream) and to the stripper 15. The pressure in the stripper 15 in maintained by control of the back pressure provided by the vapor vent from vent condenser 19. The temperature in the stripper 15 overhead is to be from about 25° C. to about 40° C. and the stripper 15 bottoms is about 120° C. to about 160° C. The rich cycle water stream can be preheated in heat exchanger 20 to reduce the duty necessary to operate the stripper 15. The pressure in the stripper 15 is maintained within a range of about 0.2 MPa to about 0.6 MPa. The stripper 15 may also utilize a steam ejector system well-known to those skilled in the art, with steam supplied from either: (1) steam generated elsewhere in the ethylene oxide production facility or (2) medium- or high-pressure steam supplied externally/OSBL; or a combination of these two sources.

As shown in FIG. 2 the pressurized stripper-overhead stream flows through conduit 30 to a condenser 16 and then to a flash drum 17 that separates the flashed light gases from the concentrated ethylene oxide aqueous liquid stream that feeds pump 18. The discharge of pump 18 splits into two streams: one stream as a reflux back to the stripper 15 and one net product liquid aqueous stream concentrated in ethylene oxide. The flashed light gases from flash drum 17 flow to a vent condenser 19 to further recover ethylene oxide from the flashed vapor stream and control the amount of dissolved light gases in the concentrated liquid ethylene oxide solution 41. Compared to the highly diluted aqueous solution found at a comparable location in the ethylene oxide recovery section of the conventional process, pressurized stripper-overhead stream is considerably more enriched in ethylene oxide, containing at least about 40 mol %, preferably at least about 50 mol % ethylene oxide with the balance of being mostly water. The pressurized stripper-overhead stream is thus supplied both at high concentrations of ethylene oxide and at high pressure. This makes the stream extremely useful for further processing into ethylene glycols via catalytic hydrolysis on a highly economical basis as the stream does not need to be further enriched or pressurized in a downstream processing steps. Another advantageous process option of the present invention is that the liquid bottoms of the stripper 15, which is a lean cycle water solution containing little ethylene oxide (from about 1 molar ppm to about 50 molar ppm) and which is also free of light components as well as impurities, may in preferable embodiments be used in a variety of other heat integration schemes elsewhere in the plant depending on need and conditions.

Under these circumstances of streams having a higher than typical ethylene oxide concentration, operators will continue to maintain appropriate safety standards that are always observed when producing, handling or storing ethylene oxide. As always, measures must be taken to prevent reactions or events that could result in ignition, combustion, deflagration, detonation or explosion of any gas stream, but especially those containing higher than typical concentrations of ethylene oxide. Accordingly, to prevent such events relief devices may be used to relieve or reduce undesirable pressure built-up in the process, reaction, or separation systems or elsewhere in the ethylene oxide plant both upstream and downstream of what is illustrated. The separation in the stripper 15 is so effective that nearly all of the ethylene oxide in the rich cycle water that enters the stripper 15 is successfully separated and recovered from the rich cycle water and leaves the stripper 15 as net liquid overhead stream while only a very small portion of EO leaves the stripper 15 elsewhere.

The pressurized stripper-overhead stream made in stripper 15 flows at elevated pressure through conduit 40 from the stripper section 1 to the reaction section 25 as previously described and shown in FIG. 2. In the present invention the reaction section 25 contains two or more reactors. In FIG. 2, a reaction section 25 is shown with a train of two adiabatic catalytic reactors arranged in series configuration each with a reactor feed heat exchanger cooler, and each reactor feed heat exchanger cooler with capability for accepting hot recycled effluent from the second reactor via pump 19. Specifically, as shown in FIG. 2 and also in more detail in FIG. 3, the reactor section 25 shows a reactor train 22 of two down-flow, fixed-bed, series-arranged adiabatic reactors, 38 and 40, each with reactor feed heat exchanger coolers 39 and 43 respectively, and recycle pump 19. The reactors are designated as the first adiabatic reactor 38 and the second adiabatic reactor 40, but as used herein these adiabatic reactors 38 and 40 may also be referred to as "reactors".

As discussed above, external cooling is necessary because the reaction of water with ethylene oxide is highly exothermic, so is it necessary to remove the heat of reaction from the product or outlet streams when the reaction occurs in adiabatic reactor as in the present invention to avoid excessive reactor bed temperature rise that can compromise the life of temperature sensitive catalyst such as ion-exchange resins. This differs from isothermal conditions where the heat of reaction is removed directly from the reactor. Maintaining the ion exchange resin catalyst at temperatures that the resin can tolerate is of course critical to reduce swelling, prevent degradation and maximize catalyst life. If operated properly the adiabatic temperature rise can be controlled to a level which maintains both good performance and life.

Lastly, positioned down-stream of the reactor train 22 is a conventional non-catalytic adiabatic pipe reactor 26 (this reactor of course contains no catalyst).

As mentioned above the concentrated ethylene oxide-water solution in conduit 40 having been made from the cooled process stream in condenser 16 is relatively cold and thus is mixed with water stream 36 that has been heated in exchanger 35 to form mixed stream 41, then is combined with the recirculation split stream 57, and cooled to a temperature sufficiently high to drive the catalytic hydration reaction of ethylene oxide to monoethylene glycol. Heat exchanger 39 brings the ethylene oxide-water solution to a temperature of between 70° C. and 100° C. Heat exchanger 35 also provides heat to achieve a temperature sufficiently high to drive the ethylene oxide hydration reaction at startup, when no hot reactor recycle stream is yet available.

The ethylene oxide-water solution 41 will comprise preferably about 5 mol % ethylene oxide to about 10 mol % ethylene oxide. Thus the ethylene oxide-water solution 41 contains a significant stoichiometric excess of water to ethylene oxide than is necessary for the hydration of ethylene oxide to ethylene glycol. In molar ratio terms, the ethylene oxide-water solution will have a molar ratio of water:ethylene oxide mole ratio of about 5:1 to about 15:1, preferably about 7:1 to about 12:1; and while this represents the aforementioned stoichiometric excess, as mentioned above, it is considerably lower than amounts used in the prior art for non-catalytic hydration. And thus, because the feedstream contains less water, the final product will also have correspondingly lower amounts of water that need to be removed from the product, as described below.

The ethylene oxide-water solution stream 41 is now supplied to the aforementioned reactor section 25 where it is combined with the recirculation split stream 57 to form a first feed stream 58. As the recirculation split stream 57 is considerably depleted in ethylene oxide compared to the ethylene oxide-water solution stream 41 supplied to the reaction section 25 the resulting first feed stream 58 will have a higher ratio of water to ethylene oxide compared to the ratio of water to ethylene oxide in the ethylene oxide-water solution stream 41, preferably a molar ratio of 40:1 to about 10:1, preferably about 30:1 to about 20:1, water:ethylene oxide. This is in the case with the two successive reactors illustrated in FIG. 2 as the amount of ethylene oxide is gradually depleted as more and more monoethylene glycol is made and the ratio of water to ethylene oxide in successive reactors increases. This is a considerable improvement over conventional operation of catalytic and non-catalytic hydration. By recirculating a portion of the reactor effluent to each reactor (steams 61 and 57), a high water:ethylene oxide ratio in the feedstream to each reactor can be obtained while simultaneously maintaining a lower overall water:ethylene oxide ratio in the product stream 88 at the end of the reactor section which is fed to the evaporators for water removal. Thus, the reaction of ethylene oxide and water is catalyzed both by the presence of ion exchange resin and the significant excess of water to ethylene oxide. This encourages monoethylene glycol production and suppression of higher glycol homolog formation—there is thus a benefit of both effects. And yet this is maintained while having a final product that is much more concentrated in ethylene glycol and thus requires far less energy in the evaporation section. For example in the present invention the final product of the reactor section, the combined reactor product 88, may have a total glycols (mono-, di-, tri- and trace higher) concentration of 20 wt % or even higher while by contrast in a conventional plant the glycol reactor effluent sent to the evaporation section has a total glycols concentration of about 12 wt %, thus reducing the amount of heat duty necessary for evaporation of the excess water has been reduced by a factor of at least 40%.

Having illustrated the overall operational scheme of the reactor section and the benefits of the present invention, the process of the present invention will now be described in further detail with continued reference to FIG. 2.

As mentioned above streams 41 and 57 are combined and cooled in heat exchanger 39 to form the feedstream 37 to the first reactor 38 and thus, the temperature of reactor 38 is regulated by controlling the temperature of stream 37, while the temperature in the successive series reactor 40 is regulated with the use of heat exchanger 43.

Regulating temperature and pressure are important parts of the process of the present invention. The hydration reaction in the present invention is carried out as a liquid phase process. In the present invention by "liquid phase process" it is meant that the feedstreams supplied to the reactor, the reactor product or reactor effluent streams, and the reactants inside the reactor are maintained in the liquid phase. Accordingly, the temperature and pressure in each reactor is such that as the streams are supplied to and enter into each reactor, they are maintained in the liquid phase. The temperature and pressure in each reactor is thus regulated to maintain the contents of the reactor in a liquid phase. The choice of temperature is largely determined by the considerations of the aforementioned paragraphs. Thus given the temperature ranges, below, in the present invention with the reactor contents being in liquid form, the pressure will be between about 7 atm to about 15 atm, preferably about 8 atm to about 13 atm.

In selecting the temperature two competing requirements must be balanced. First, as mentioned above the temperature of the inlet in the present invention must be sufficiently high to drive the hydration reaction of ethylene oxide so that there is significant conversion of ethylene oxide to monoethylene glycol. In the present invention the conversion percentage of ethylene oxide to monoethyelene glycol in the first reactor should be at least about 50%, preferably at least about 60% of the total ethylene oxide reacted. Thus, the temperature at the inlet to the first reactor 38 must be within the range of about 50° C. to about 90° C., preferably within the range of about 70° C. to about 85° C. The conversion percentage of ethylene oxide to monoethyelene glycol in the second reactor 40 should be about at least 10% of the total EO reacted, preferably at least about 20% of the total EO reacted. Thus, the temperature at the inlet to the second adiabatic reactor 40 must be within the range of about 70° C. to about 110° C., preferably within the range of about 80° C. to about 95° C. However, the temperature in the reactor (and consequently at the reactor outlet) should not be too high because, as mentioned above, a significantly high temperature inside the reactor causes swelling and degradation of the ion exchange resin. High temperatures in the reactor are the result of the exothermic hydration reaction and so to moderate any temperature increase this heat of reaction must be removed. In prior art isothermal operations the heat of reaction can be removed, e.g., by absorption into a shell-side coolant. This is not possible with the adiabatic reactors of the present invention, which have considerably less process complication but are correspondingly less versatile in their heat removal capacities. However, in the present invention it has been discovered that the temperature rise can nonetheless be at least partially moderated within a range suitable for stable operation of the ion exchange resin catalyst by the superabundant water in each reactor which acts as a heat sink. Thus, while one goal of the present invention is to reduce the amount of water used in the production of ethylene glycol, nonetheless at least a minimum amount of water is necessary to moderate the temperature increase in the reactors arising from the exothermic reaction. As described above, both of these goals are met in the present invention by recirculating portions of the catalytic reactors effluent 74 to the same reactors 38 and 40. With this inventive configuration a progressively higher water:ethylene oxide ratio is obtained inside successive reactors moderating the exotherm so that at the outlet of each reactor the temperature is between about 90° C. to about 120° C., preferably between about 95° C. to about 110° C.

Despite the success of the present invention at moderating the temperature rise in the reactor it may nonetheless be necessary to reduce the reactor effluent temperature still further until reaching the acceptable inlet temperature range mentioned above. In order to do this the combined streams 58 and 62, including streams 57 and 61, are passed through heat exchangers 39 and 43, respectively. This presents an opportunity for heat integration as a flow stream (not pictured) from outside the reaction section may be heated in any of the heat exchangers by indirect heat exchange with the reactor effluent from one or more of the series reactors.

As noted above, at higher temperatures there is nearly complete conversion of ethylene oxide to monoethylene glycol—at lower inlet temperatures not all of the ethylene glycol will react and detectable amounts of ethylene oxide will appear and remained unreacted ("break through") in the reactor effluent. In certain situations it may be desired to reduce the inlet temperature in order to reduce the ethylene oxide conversion to allow for more ethylene oxide breakthrough—when for example it is desired to extend the life of the ion exchange resin catalyst or in other situations, as described below.

In addition to the above-mentioned parameters and operating conditions, other factors that may be considered when operating the process include but are not limited to: reactor and process configuration, the conversion rate and selectivity of the ion exchange resin catalyst, and reactants flow rate (LHSV).

With the aforesaid considerations in mind, feed stream 41 combines with the recirculation split stream 57 in a volume ratio of stream 41:stream 57 of about 0.5:1 to about 2:1. The resulting first feed stream 58, after being cooled to sufficient reaction temperature in heat exchanger 39, enters reactor 38 where the ethylene oxide reacts with water in the presence of an ion exchange resin catalyst or catalyst bed to form monoethylene glycol. In the adiabatic reactors of the present invention, e.g., reactor 38, mixing ethylene oxide with excess water at or above the catalytic temperature in the presence of the catalyst results in the hydration of ethylene oxide that is highly selective to monoethylene glycol so that at least about 95%, preferably at least about 98% of the ethylene oxide that is converted is converted to monoethylene glycol with only small percentages being converted into higher glycols like diethylene glycol or triethylene glycol (conversion percentages are mentioned above). In addition to the monoethylene glycol product, each effluent of the reactors in the present invention contains water and ethylene oxide (the excess amounts available for recirculation to the same reactor or for further addition into the next reactor), and trace quantities of other components including ethylene oxide and higher glycol homologs.

Leaving reactor 38, effluent stream 70 is combined with recirculated effluent stream 61 in a volume ratio of stream 70:stream 61 of about 0.5:1 to about 2:1. The combined stream 62 is then passed through heat exchanger 43, where it is cooled to form stream 81 for feeding into reactor 40. In the second adiabatic reactor 40 as in reactor 38 the ethylene oxide reacts with water at a high selectivity and conversion rate so that the second reactor effluent stream 73 like the first reactor effluent contains unreacted water and ethylene oxide as well as monoethylene glycol and the trace components mentioned above. The second reactor effluent stream 73 is removed from the second adiabatic reactor 40, pressurized in pump 19 and is subsequently divided between a forward stream 76 and a recirculation stream 75, which itself is subsequently divided into recirculation split stream 57 and recirculation supply stream 61. Essentially the only difference between 70 and 73 is that the latter contains more monoethylene glycol because it contains the amount of monoethylene glycol that is produced in both reactors 38 and 40 and accordingly contains significantly less ethylene oxide.

Both the first feed stream 58 and the combined stream 62 are each passed through their respective heat exchangers 39 and 43 to ensure the streams are at acceptable temperatures. In this case, heat exchanger 43 functions like heat exchanger 39, cooling the reactor feed stream for sufficient control of the catalytic reaction.

In addition to the previously described reactor train encompassing the two down-flow, fixed-bed series reactors, the reactor section 25 also includes a conventional pipe reactor 26 to which the forward stream 76 may be supplied. In the present invention this pipe reactor 26 is configured and operated to provide hitherto unknown levels of versatility and operability to a catalytic hydration process scheme, which shall now be described in more detail.

First, in addition to increasing the conversion and selectivity of the reaction of ethylene oxide and water to MEG, the present invention may also be operated and configured to increase the versatility and adaptability of the hydration process by allowing the process operator to make di- and triethylene glycol. This can be done by physically bypassing one or more of the catalytic reactors 38 and 40 (this bypass itself is not illustrated) and thereby removing the one or more catalytic reactors from the circulation of the feedstream. The ethylene oxide that "breaks through", or remains unreacted, after by-passing one or more of the aforementioned catalyst reactors is sent to the non-catalytic pipe reactor 26 for thermal conversion of ethylene oxide and water to ethylene glycol. As the pipe reactor 26 is non-catalytic and relies entirely on thermal conversion the forward stream 76 is preheated in heat exchanger 55 to arrive at pipe reactor feed stream 77 within the effective temperature range for non-catalytic hydration of ethylene oxide into monoethyelene glycol—preferably the inlet temperature of the pipe reactor 26 is from about 130° C. to about 160° C.

Of course this non-catalytic thermal conversion is significantly less selective to MEG, with substantial amounts of higher glycols such as DEG and TEG also produced so that by increasing the amount of ethylene oxide that is converted into ethylene glycol in the pipe reactor, the reactor product 88 contains less MEG and more DEG and TEG than would be produced if only the catalytic reactors in the reaction section 25 were being used. This provides the operator a versatile and flexible process for ethylene glycol production as the output of mono-, di- and triethylene glycol product may be adjusted by the operator to meet demand. In a limiting case, all catalytic reactors are bypassed so that only the final non-catalytic pipe reactor 26 is left and all hydration will occur in this reactor—thus converting the catalytic process into a non-catalytic one.

Alternatively, rather than physically bypassing the reactors, a "temperature bypass" can be effected by reducing the inlet temperature to one or more of the catalytic reactors as low as desired to reduce the reaction between the ethylene oxide and water and thus reducing the amount of monoethylene glycol made in the reactors, meaning more unreacted ethylene oxide "breakthrough" is seen in the outlets of the catalytic reactors. This ethylene oxide is then converted to ethylene glycol in the pipe reactor as set forth above.

The pipe reactor may also function in a "finishing" role. Even when the train of reactors 22 is operating within normal catalytic efficiency as designed to maximize the conversion of ethylene oxide to ethylene glycol, nonetheless a small amount of unreacted ethylene oxide will remain unreacted through all reactors in train 22 and this ethylene oxide will "breakthrough" in the forward stream 76. In the present invention train 22 is preferably operated so that the concentration of ethylene oxide in the forward stream 76 will be no greater than about 1 mol %. This remaining ethylene oxide can then be converted to monoethylene glycol in the pipe reactor 26. The use of the pipe reactor as a finishing reactor can have significant economic benefit by reducing the required quantity of catalyst. The small conversion of ethylene oxide achieved in the pipe reactor is done at very high excess of water, such that the selectivity to monoethylene glycol over higher glycols is very close to that of the catalytic reactors. The required catalyst quantity and catalytic reactor volume is therefore greatly reduced, while still maintaining a very high overall selectivity to monoethylene glycol.

Finally, the pipe reactor 26 can also be used as a stand-by reactor in situations where one or more of the catalytic reactors malfunctions or has to be otherwise removed from service because of exhaustion, a blockage in the resin bed or nozzle or some other difficulty commonly observed in operation of ion exchange resin beds. When this happens the malfunctioning catalytic reactor must be taken out of service. This means that there will be excess unconverted ethylene oxide in the reaction section 22 which is undesirable. This excess ethylene oxide breakthrough can be converted into ethylene glycol in the pipe reactor 26. Thus, the presence of the pipe reactor 26 in the present prevention provides considerable flexibility and operability for the process operator. Unlike in the prior art where the inability to replace or repair the ion exchange resin catalyst or reactor is a serious disadvantage of solid/heterogeneous catalytic systems, in the present invention reactors may be taken offline for such repair without interrupting operation.

Figure 3:
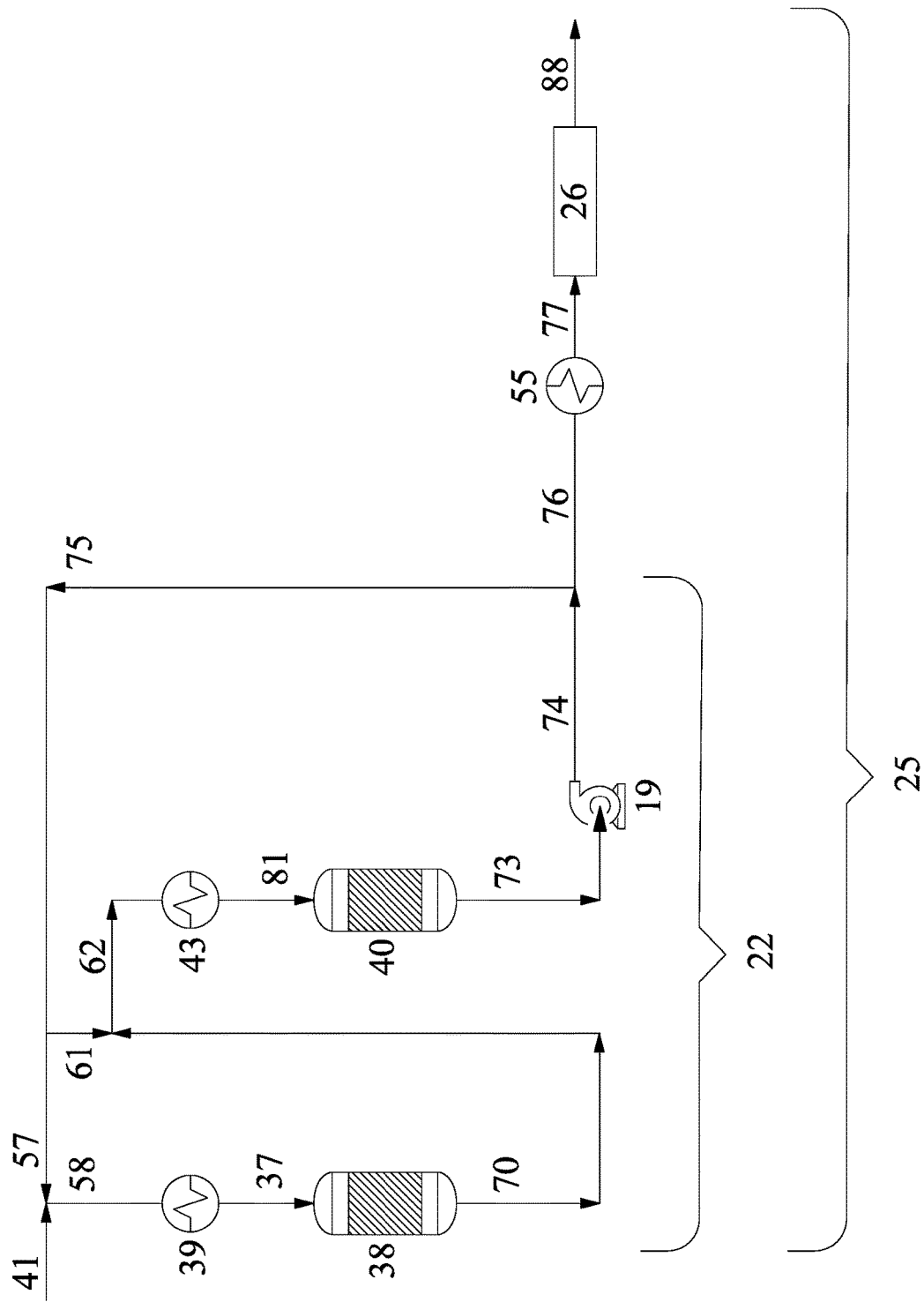

While two reactors and two heat exchangers are shown in the reactor section of FIGS. 2 and 3, this is for purposes of illustration only. More reactors may be used depending on specific needs and requirements. Increasing the number of reactors has the advantage of reducing the exotherm across each reactor—thus moderating the amount of temperature-induced irreversible swelling the ion exchange resin catalyst experiences inside each reactor. Additionally, increasing the number of reactors also increases the dilution of the ethylene oxide, and because ethylene oxide degrades most ion exchange resins increased dilution is expected to extend resin life.

The primary drawbacks of more reactors is cost and complexity including the additional capital cost of reactors, pumps, exchangers and other equipment as well as the operating costs of larger volumes of ion exchange resin catalyst as well as additional piping, instrumentation and operational complexity.

The alkylene glycol in the combined reactor product 88 can then be recovered by a multi-effect evaporator or vacuum distillation, or any other suitable means known to those skilled in the art. Recovery techniques can be combined for different stages in the recovery. For example, the multi-effect evaporator can be used to remove water from the reactor effluent while vacuum distillation can be used for glycol drying. Indeed, it is one of the benefits of the present invention that in the post-glycol reaction section of the plant, complexity can be reduced because the amount of heat duty necessary for evaporation of the excess water has been reduced as noted above. Thus, while prior art plants often incorporate evaporation systems having several effects or stages (see e.g., EP No. 2121646 B1) the present invention requires fewer number of stages.

As discussed above, the present invention may involve one or more ion exchange resin catalysts. Ion exchange resins have a polymer matrix which contain on the surface ion exchanging sites populated by ionic functional groups. Ion exchange resins are typically differentiated between cationic or anionic exchange resins, although other types of ion exchange resins are also available. For a more comprehensive description of cation- and anion-exchange resins see, de Dardel, F. and Arden, T. V. *Ion Exchangers in Ullman's Encyclopedia of Industrial Chemistry* (2005).

Suitable polymer matrices for the ion exchange resin catalysts include a polystyrene matrix, a polyacrylic matrix, a polyalkylamine resin as well as other polymeric materials. Preferably, the polymer matrix is cross-linked with divinylbenzene to a sufficient degree to increase the operating capacity while also not increasing the density of the ion exchange material to such an extent that the ion exchange material becomes too physically hard and too chemically resistant to chemical treatment. Preferably the matrix is a styrene, divenylbenzene co-polymer.

Fixed to sites on the polymer matrices described above are ionic stationary groups that determine whether the resin functions as a cationic or anionic ion exchange resin. In solutions, the positive or negative charge of the stationary groups is compensated for by ions of opposite charge which are referred to herein as the functional group.

Strongly acidic cationic ion exchange resins typically include sulfonic groups as stationary groups in turn attached to a styrene-divenylbenzene polymer matrix. Examples of strongly acidic sulfonic cation-exchange resins include Amberlite IR 120, Dowex HCR, Lewatit S 100, and Amberlyst 15, among others.

Cationic ion exchange resins may also include the resin material that is the copolymer obtained by the addition polymerization of an acrylic or methacrylic acid and divinylbeneze such as disclosed in U.S. Pat. No. 3,957,698. Other suitable polymer materials for cationic exchange resins include the resin matrix formed when polyvinylpyridine resin cross-linked with divenylbenzene. Such materials are available under the Reillex HPQ trademark. Sulfonated phenolic polymer resins are also suitable cationic ion exchange resins.

Weakly acidic cationic ion exchange resins typically include carboxylic groups as stationary groups. Examples of weakly acidic cation-exchange resins include Amberlite IRC 86, Dowex Mac-3, Lewatit CNP, among others.

As used herein in the present invention, strongly basic anionic exchange resins contain quaternary ammonium stationary groups. These are further divided into Type I, made by the reaction of trimethylamine with the styrene-divenylbenzene copolymer after chloromethylation, and Type II obtained by the reaction of the styrene-divenylbenzene copolymer with dimethylethanolamine. Suitable examples of such Type I resins include Lewatit MP 500 available from Lanxess, and Amberlyst 26 and Amberlite IRA 402, and IRA 410 available from Dow. Suitable examples of strongly basic Type II resins include, e.g., Purolite A510S (Purolite Corporation).

Weakly basic anion exchange resins typically include polyacrylic resins provided with stationary groups by reaction with a polyfunctional amine to result in anion exchange resins such as the tertiary ammonium weakly basic Amberlite IRA 67 and Amberlyst 21 resins (available from Dow). It should be especially noted that this ion exchange resin can be then be further treated with chloromethane or dimethyl sulfate to give a quaternary amine strongly basic Type I resin Amberlite IRA 458 resin (Dow). Weakly basic anion exchange resins may also include a free base group as the stationary group such as the Amberlite IRA-67 resin (Dow).

In a particular embodiment of the present invention the strongly basic anionic exchange resin contains a "linking" group of 3-7 linking atoms, preferably 3-5 carbon atoms between the quaternary ammonium stationary group and the benzene group of the polymer matrix/material. An example of such a linking chain in a strong base resin is illustrated in U.S. Pat. No. 5,945,568 and was produced under the name Diaion TSA1200 (Mitsubishi Chemical). As specified in the '568 patent the linking group which links the quaternary ammonium stationary group to the benzene group of the polymer matrix is not particularly limited as long as it is sufficiently long. Suitable examples of the linking group are an alkylene group or an alkyleneoxyalkylene group. A preferred example for use in the present invention is an anion exchange resin which comprises, as the substrate, a polymer of a vinyl aromatic compound and which has a structure such that a quaternary ammonium group is bonded to the aromatic group via a linking group having a chain length of at least 3.

Without being limited by theory it is believed that in the present invention this linking group prevents the nucleophilic attack on the ammonium stationary group from the benzene ring which otherwise would lead to accelerated deactivation and degradation of the ion exchange resin catalyst and reduced stability and catalyst life.

A variety of ions are suitable for use as the functional group in anionic resins of the present invention and may be selected from the group including bicarbonate, carbonate, hydroxide, bisulfite, carboxylate, citrate, and metalate, and molybdate anions. These functional groups may be used with any of the stationary groups and resin material identified above.

In the present invention it is preferred that the ion exchange resin catalyst is from the group of type I strongly basic anion exchange resins, more preferably type I strongly basic anion exchange resins with a bicarbonate or monocitrate functional group, and most preferably type I strongly basic anion exchange resins with a bicarbonate or monocitrate functional group with a linking group.

In addition to the ion exchange materials specified above, any other suitable cationic or anionic exchange resin may be used such as the cation- and anion-exchange resins set forth above in de Dardel, F. and Arden, T. V. 2008, *Ion Exchanger, in Ullman's Encyclopedia of Industrial Chemistry.*

In addition to the aforementioned ion exchange material it is also possible to use a combination of a homogeneous and heterogeneous catalyst—for example a solid catalyst on which is adsorbed a soluble metallic catalyst. In this case, first a solid catalyst having a metallic catalyst adsorbed on it is prepared. Then, during the liquid-phase hydration reaction described above, the metallic catalyst is desorbed from the solid catalyst and can effectively catalyze the reaction. The metallic catalyst must then be separated from the reaction products and can be reused for re-adsorbing on to the solid catalyst. The solid catalyst in this case can be an ion exchange resin.

The above paragraphs concern the selection of suitable ion exchange resin catalysts for use in the catalytic reactors of the present invention. With respect to the operation of the ion exchange resin-containing catalytic reactors, in FIGS. 2 and 3 the feedstream travels in a direction from the top of the reactor downwards through each of the reactors. This is referred to as "down-flow" mode, but in the present invention the reactors may be operated in either "down-flow" or "up-flow" modes. Down-flow mode processes have the advantage of increasing the density of catalyst within the reactor and thereby reducing the size and cost of the reactors themselves. Down-flow operations also minimize the non-catalytic reaction of water and ethylene oxide to ethylene glycol. However, during the course of down-flow operation catalyst selectivity may be impaired both by local inhomogeneities and impurities that may develop and become entrapped in the catalyst bed and by "channeling" that develops in the catalyst bed.

As can probably be surmised, in up-flow operation the feedstream travels in a direction from the bottom of the reactor upwards. In PCT Publication No. WO2008/150338A1 increased stability and operational life of ion exchange resin in up-flow operational mode was reported. In the present invention with liquid-phase reactants and a solid catalyst up-flow operation may provide a modest amount of bed fluidization during up-flow operation which increases the void fraction between adjacent resin particles allowing for the reduction of the inhomogeneities and contaminates that otherwise become embedded and trapped in the catalyst bed during down-flow operation and degrade catalyst performance. U.S. Pat. No. 6,160,187 has previously disparaged up-flow operation of catalytic reactors because the resulting bed fluidization purportedly causes greater catalyst attrition and reduced monoethylene glycol selectivity due to axial mixing. However, it has been discovered in the present invention that in the liquid phase process of the present invention these criticisms are not realistic because they are more likely to occur in gas/solid catalyst systems where there are much higher velocities, a greater difference in densities (between the gas reactant and solid catalyst compared to a liquid reactant and solid catalyst), and thus a much greater bed expansion than in the present liquid/solid catalyst system of our invention. Thus, up-flow operation remains a suitable mode of operation in the present invention.

Silver-Based Epoxidation Catalyst

The silver-based epoxidation catalyst includes a support, and at least a catalytically effective amount of silver or a silver-containing compound; also optionally present is a promoting amount of rhenium or a rhenium-containing compound; also optionally present is a promoting amount of one or more alkali metals or alkali-metal-containing compounds. The support employed in this invention may be selected from a large number of solid, refractory supports that may be porous and may provide the preferred pore structure. Alumina is well known to be useful as a catalyst support for the epoxidation of an olefin and is the preferred support.

Regardless of the character of the support used, it is usually shaped into particles, chunks, pieces, pellets, rings, spheres, wagon wheels, cross-partitioned hollow cylinders, and the like, of a size suitable for employment in a fixed-bed epoxidation reactor. The support particles will preferably have equivalent diameters in the range from about 3 mm to about 12 mm, and more preferably in the range from about 5 mm to about 10 mm. (Equivalent diameter is the diameter of a sphere having the same external surface (i.e., neglecting surface within the pores of the particle) to volume ratio as the support particles being employed.) Suitable supports are available from Saint-Gobain Norpro Co., Sud Chemie AG, Noritake Co., CeramTec AG, and Industrie Bitossi S.p.A. Without being limited to the specific compositions and formulations contained therein, further information on support compositions and methods for making supports may be found in U.S. Patent Publication No. 2007/0037991.

In order to produce a catalyst for the oxidation of an olefin to an olefin oxide, a support having the above characteristics is then provided with a catalytically effective amount of silver on its surface. In one embodiment, the catalytic effective amount of silver is from 10% by weight to 45% by weight. The catalyst is prepared by impregnating the support with a silver compound, complex or salt dissolved in a suitable solvent sufficient to cause deposition of a silver-precursor compound onto the support. Preferably, an aqueous silver solution is used.

A promoting amount of a rhenium component, which may be a rhenium-containing compound or a rhenium-containing complex may also be deposited on the support, either prior to, coincidentally with, or subsequent to the deposition of the silver. The rhenium promoter may be present in an amount from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Other components which may also be deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of support, silver, alkali metal promoter(s), rhenium component, and optional additional promoter(s) of the instant invention will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably, the amount ranges from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof.

The amount of alkaline earth metal promoter(s) and/or transition metal promoter(s) deposited on the support is a promoting amount. The transition metal promoter may typically be present in an amount from about 0.1 micromoles per gram to about 10 micromoles per gram, preferably from about 0.2 micromoles per gram to about 5 micromoles per gram.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Organic-based solvents which have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range from about 0.1% by weight up to the maximum solubility afforded by the particular solvent/solubilizing agent combination employed. It is generally very suitable to employ solutions containing from 0.5% to about 45% by weight of silver, with concentrations from 5 to 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution. Impregnation procedures are described, for example, in U.S. Pat. Nos. 4,761,394, 4,766, 105, 4,908,343, 5,057,481, 5,187,140, 5,102,848, 5,011,807, 5,099,041 and 5,407,888. Known prior procedures of pre-deposition, co-deposition and post-deposition of various the promoters can be employed.

After impregnation of the support with the silver-containing compound, i.e., a silver precursor, a rhenium component, an alkali metal component, and the optional other promoters, the impregnated support is calcined for a time sufficient to convert the silver containing compound to an active silver species and to remove the volatile components from the impregnated support to result in a catalyst precursor. The calcination may be accomplished by heating the impregnated support, preferably at a gradual rate, to a temperature in the range from about 200° C. to about 600° C. at a pressure in the range from about 0.05 to about 3.5 MPa. In general, the higher the temperature, the shorter the required heating period. A wide range of heating periods have been suggested in the art; e.g., U.S. Pat. No. 3,563,914 discloses heating for less than 300 seconds, and U.S. Pat. No. 3,702, 259 discloses heating from 2 to 8 hours at a temperature of from 100° C. to 375° C., usually for duration of from about 0.5 to about 8 hours. However, it is only important that the heating time be correlated with the temperature such that substantially all of the contained silver is converted to the active silver species. Continuous or step-wise heating may be used for this purpose.

During calcination, the impregnated support may be exposed to a gas atmosphere comprising an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcination. Further information on catalyst manufacture may be found in the aforementioned U.S. Patent Publication No. 2007/0037991.

For purposes of illustration only, the following are conditions that are often used in current commercial ethylene oxide reactor units: a gas hourly space velocity (GHSV) of 1500-10,000 h$^{-1}$, a reactor inlet pressure of 1 MPa to 3 MPa, a coolant temperature of 180-315° C., an oxygen conversion level of 10-60%, and an EO production rate (work rate) of 100-350 kg EO/m$^3$ catalyst/hr and a change in ethylene oxide concentration, ΔEO, of from about 1.5% to about 4.5%. The feed composition in the reactor inlet after the completion of start-up and during normal operation typically comprises (by volume %) 1-40% ethylene, 3-12% $O_2$; 0.2% to 10%, preferably 0.2% to 6%, more preferably 0.2% to 5% of $CO_2$; 0-5% ethane, an amount of one or more chloride moderators, which are described herein; and the balance of the feed being comprised of argon, methane, nitrogen or mixtures thereof.

We claim:

1. A liquid phase process for the production of ethylene glycol comprising:
    providing an ethylene oxide-water solution stream containing ethylene oxide and water;
    combining the ethylene oxide-water solution stream with a recirculation split stream to form a first reactor inlet stream;
    supplying the first reactor inlet stream to an inlet of a first adiabatic reactor, the inlet of the first adiabatic reactor being at a first inlet temperature, wherein the first reactor inlet stream is cooled to the first inlet temperature, prior to being supplied to the inlet of the first adiabatic reactor, by a heat-exchanger that is located upstream from the first adiabatic reactor;
    reacting the ethylene oxide and water contained in the first reactor inlet stream in the presence of a first ion exchange resin catalyst in the first adiabatic reactor to produce an effluent stream containing water, ethylene glycol, and unreacted ethylene oxide;
    further combining the effluent stream with a recirculation supply stream to form a combined stream containing water, ethylene glycol and unreacted ethylene oxide;
    supplying the combined stream to an inlet of a second adiabatic reactor, the inlet of the second adiabatic reactor being at a second inlet temperature;
    reacting ethylene oxide and water contained in the combined stream in the presence of a second ion exchange resin catalyst in the second adiabatic reactor to produce a second reactor effluent stream containing water, ethylene glycol, and unreacted ethylene oxide;
    compressing the second reactor effluent stream;
    dividing the second reactor effluent stream into a recirculation supply stream and a forward stream;
    dividing the recirculation stream into the split recirculation stream and the recirculation supply stream; and
    supplying the forward stream to a non-catalytic pipe reactor to produce a product stream wherein the total concentration of diethylene glycol (DEG), triethylene glycol (TEG) and higher glycols in the product stream is greater than the total concentration of DEG, TEG and higher glycols in the forward stream.

2. The liquid phase process according to claim 1, wherein the non-catalytic pipe reactor has an inlet temperature from about 130° C. to about 160° C.

3. The liquid phase process according to claim 1, wherein each of the first inlet temperature and the second inlet temperature is from about 50° C. to about 90° C.

4. The liquid phase process according to claim 1, wherein the first adiabatic reactor has a first outlet temperature and the second adiabatic reactor has a second outlet temperature, wherein each of the first outlet temperature and the second outlet temperature is from about 90° C. to about 120° C.

5. The liquid phase process according to claim 1, wherein the first reactor inlet stream has a molar ratio of water:ethylene oxide of from about 40:1 to about 10:1.

6. The liquid phase process according to claim 5, wherein said molar ratio of water:ethylene oxide in the first reactor inlet stream is from about 30:1 to about 20:1.

7. The liquid phase process according to claim 1, conducted continuously.

8. The liquid phase process according to claim 1, wherein a total molar ratio of water:ethylene oxide in the ethylene oxide-water solution stream is about 5:1 to about 15:1.

9. The liquid phase process according to claim 1, wherein a total molar ratio of water:ethylene oxide in the ethylene oxide-water solution stream is about 7:1 to about 12:1.

10. The liquid phase process according to claim 1, wherein the concentration of ethylene oxide in the forward stream is no greater than about 1 mol %.

11. The liquid phase process according to claim 1, wherein a conversion percentage of ethylene oxide to monoethyelene glycol in the first adiabatic reactor is at least about 50%.

12. The liquid phase process according to claim 1, wherein the ethylene oxide-water solution stream comprises a combination of an aqueous ethylene oxide feed stream and a water stream, wherein the aqueous ethylene oxide feed stream is prepared according to the following steps:
    providing a rich cycle water stream containing ethylene oxide, methane, ethylene, and other dissolved light gases;
    separating, in a flash drum, a light gas solute vapor from the rich cycle water stream;
    directing upwardly the light gas solute vapor through an opening in the flash drum allowing fluid communication to an absorber affixed to flash drum to form an absorber vapor overhead;
    pumping and heating the rich cycle water from a liquid bottoms of the flash drum to a stripper; and
    separating into: (1) an enriched overhead stripper liquid stream comprising at least about 40 mol % ethylene oxide, and (2) a lean cycle water solution in a stripper bottoms containing about 5 to about 50 molar ppm ethylene oxide in the stripper bottoms.

13. The liquid phase process according to claim 12, wherein said enriched overhead stripper liquid stream comprises at least about 50 mol % ethylene oxide.

14. The liquid phase process according to claim 1, wherein the ion exchange resin catalyst present in both the first adiabatic reactor and the second adiabatic reactor is a type I strongly basic anion exchange resin.

15. The liquid phase process according to claim 1, wherein the ion exchange resin catalyst present in both the first adiabatic reactor and the second adiabatic reactor has a bicarbonate or monocitrate functional group.

16. The liquid phase process according to claim 1, wherein the ion exchange resin catalyst present in both the first adiabatic reactor and the second adiabatic reactor includes a linking group.

17. The liquid phase process according to claim 1, wherein the first reactor inlet stream and the combined stream are substantially free of carbon dioxide.

\* \* \* \* \*